United States Patent [19]
Saulson

[11] Patent Number: 5,482,707
[45] Date of Patent: Jan. 9, 1996

[54] FLAVORED, READY TO USE ACTIVATED CHARCOAL ANTIDOTE

[75] Inventor: Saul S. Saulson, Franklin, Mich.

[73] Assignee: Frank W. Kerr Chemical Company, Novi, Mich.

[21] Appl. No.: 290,694

[22] Filed: Aug. 15, 1994

[51] Int. Cl.$^6$ .................................................. A61K 33/44
[52] U.S. Cl. .................................................. 424/125
[58] Field of Search ........................................ 424/125

[56] References Cited

U.S. PATENT DOCUMENTS

| | | | |
|---|---|---|---|
| 3,620,770 | 10/1971 | Harvey | 99/138 |
| 3,717,476 | 2/1973 | Harvey | 99/138 |
| 3,917,821 | 11/1975 | Manes | 414/125 |
| 4,122,169 | 10/1978 | Geils | 424/125 |
| 4,594,249 | 6/1986 | Procter et al. | 424/125 |
| 4,921,713 | 5/1990 | Fowler | 426/85 |
| 5,236,415 | 8/1993 | Stallings | 604/54 |

*Primary Examiner*—José G. Dees
*Assistant Examiner*—Samuel Barts
*Attorney, Agent, or Firm*—Gifford, Krass, Groh, Sprinkle, Patmore, Anderson & Citkowski

[57] ABSTRACT

To provide a therapeutic dose of an aqueous slurry of activated charcoal to a poisoning victim, an opaque straw is coated internally with a viscous flavoring solution and the slurry is sucked up from an opaque container using the straw. The use of natural and/or artificial sweeteners in the slurry masks the gritty particles and improves the taste.

7 Claims, 1 Drawing Sheet

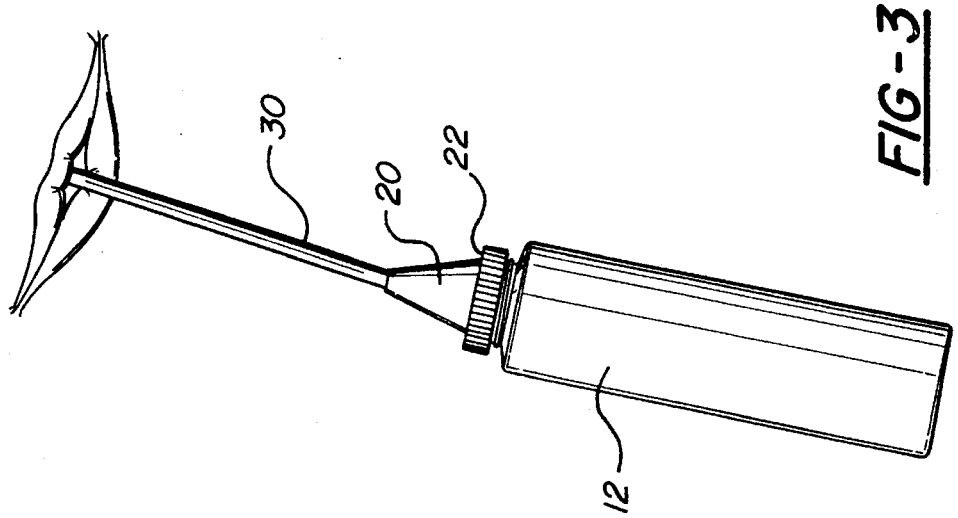
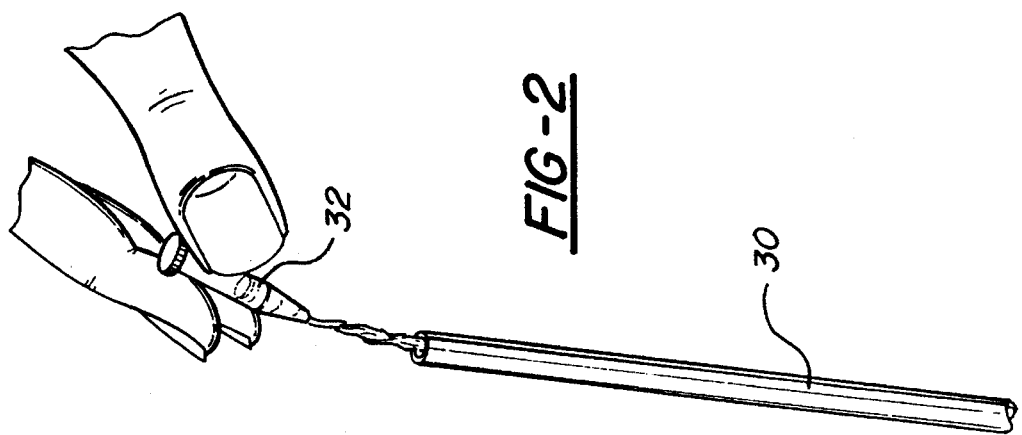
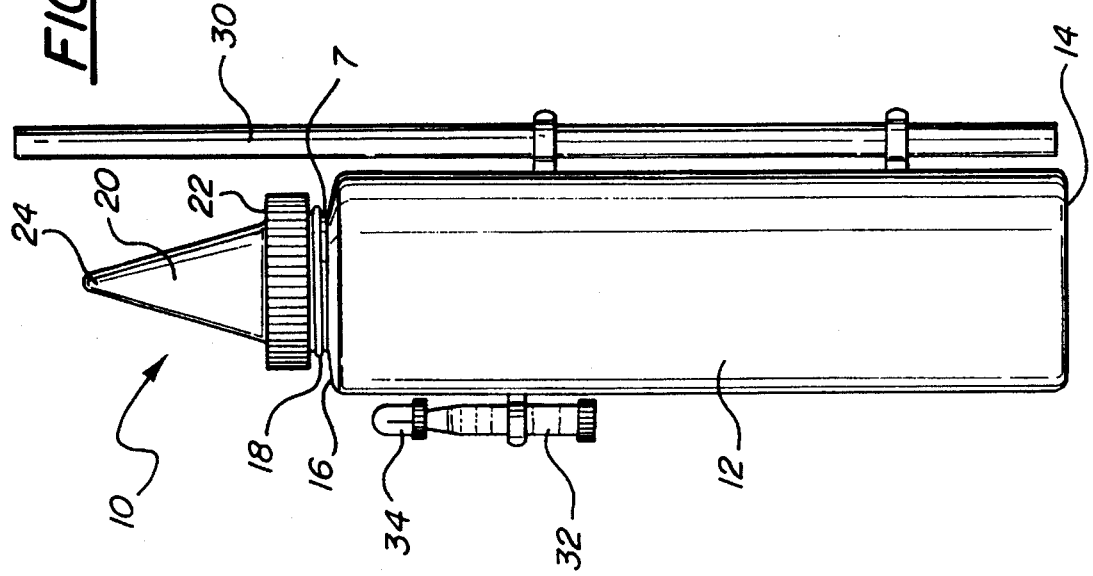

FLAVORED, READY TO USE ACTIVATED CHARCOAL ANTIDOTE

FIELD OF THE INVENTION

This invention relates to a method and apparatus for administering an aqueous slurry of activated charcoal to a poisoning victim for therapeutic purposes and more particularly to such a method and apparatus which provides flavoring to ameliorate the unpleasant taste of the charcoal slurry.

BACKGROUND OF THE INVENTION

The administration of an aqueous slurry of activated charcoal has been recognized as an effective treatment for acute toxic ingestion. The activated charcoal is a highly efficient, non-specific absorbent of a large variety of toxic substances. This treatment may be effected by non-skilled personnel in the home or workplace or it may be administered by skilled medical personnel in an emergency medical facility, poison control center or the like.

A major drawback to this use of activated charcoal has been its unpleasant appearance and flavor and unpalatable grainy texture. These factors have often caused children and adults to spew out or vomit the suspension, limiting its effectiveness and creating cleanup problems.

To eliminate the untoward effects of the unpleasant appearance of the black charcoal suspension, I developed a container system for administration as disclosed in U.S. patent application Ser. No. 08/238,969 in which a prepared mixture of activated charcoal suspension is provided in an opaque container and ingested through use of an opaque straw so that the patient does not observe the black color.

The obvious solution to the unpleasant flavor of the activated charcoal slurry would be to incorporate a pleasant flavoring component but the highly absorbent nature of the charcoal causes it to complex with these flavoring materials thus eliminating the flavor. Efforts to overcome the grittiness and sweeten the product by adding natural sugars such as dextrose were unsuccessful because to avoid bacterial and mold growth in the suspension the concentration of dextrose must be such as to make the sweetened suspension too thick to draw through a straw.

The present invention is accordingly directed toward a method and apparatus for administering an aqueous charcoal slurry that overcomes the grittiness and unpleasant flavor of the plain slurry, masks the unpleasant appearance of the charcoal, yet is simple to administer and low in cost.

SUMMARY OF THE INVENTION

The present invention solves the problem of the activated charcoal complexing with a flavoring material so as to make the flavoring effort non-effective, by providing a delivery system including a container of an aqueous slurry of activated charcoal, a straw which may be inserted into the container and used by the patient to orally suck up and drink the slurry, and a separate container of a small quantity of flavoring. The flavoring is intended to be dispensed into the interior of the straw before the straw is used to suck up the suspension and the flavoring has sufficient viscosity so as to coat the interior of the straw. When the patient sucks the emulsion through the straw some of the flavoring which has not contacted or has sufficient time to complex with the slurry is drawn along into the patient's mouth and flavors the suspension. Preferably the suspension, in the container, is sweetened with a natural sugar such as sucrose or dextrose, and/or with a non-sugar synthetic sweetener such as sorbitol which acts as a cathartic. These sweeteners tend to coat the charcoal particles so as to minimize the perception of grittiness.

The preferred suspension further includes appropriate preservatives such as methylparaben, propylparaben and/or sodium benzoate. The pH of the slurry is reduced to an acidic level by the addition of citric acid or other appropriate acids.

The charcoal slurry is preferably contained in a cylindrical plastic body having a conical top which can act as a spout. The delivery tip end of the spout may be cut off to allow the straw to be inserted. After insertion of the straw into the container of charcoal slurry, a small container of flavoring with a narrow delivery spout is inserted into the straw and the flavoring is dispersed so as to coat the interior of the straw. Both the straw and the flavor container are preferably packaged with the cylindrical bottle of slurry.

Other objects, advantages and applications of the present invention will be made clear by the following detailed description of a preferred embodiment to the invention. The description makes reference drawings in which:

BRIEF DESCRIPTION OF DRAWINGS

FIG. 1 is an illustration of a cylindrical container for the activated charcoal suspension with a straw and a vial of fluid flavoring attached to the container;

FIG. 2 illustrates the manner of the application of the flavoring into the interior of the straw; and FIG. 3 illustrates the manner of use of the flavored straw to allow a patient to suck up and drink the activated charcoal.

DETAILED DESCRIPTION OF THE PREFERRED EMBODIMENT

A dispensing container for an aqueous suspension of activated carbon or charcoal, generally indicated at 10, is formed of a cylindrical body of high density polyethylene or similar plastic material which is manually deformable to impose pressure on the contents of the body but which resiliently returns to its original cylindrical configuration when the pressure is removed. The bottle has one flat, integral end 14 and the other end is formed with a normally extending shoulder 16 and a central threaded projection 18 surrounding the mouth of the bottle 7.

The second section of the bottle consists of a conical member 20 preferably molded of the same material as the cylindrical body 12. The conical end member 20 has a base section 22 formed with internal threads complementary to the threads 18 on the mouth of the bottle 7 so that the conical end can screw on the bottle to form an integrated structure. The far end of the section 20 terminates in a closed tip 24 that seals the bottle for storage purposes.

The bottle 12 is filled with an aqueous suspension of activated carbon of very small particle size, with 75% of the material having a particle size of between 10 and 74 microns. The preferred composition of the slurry composition for use in a 12 ounce container, providing a sufficient dosage for an adult, is as follows:

1) DI water 130ml
2) dissolve methylparaben NF 0.228%, propylparaben NF 0.112%, sodium benzoate NF 0.10%
3) Dextrose monohydrate, 45gms 4) Fructose powder 32gms 5) Activated charcoal 50gms 6) QS with to 240ml 7) Titrate to pH 4.0 with citric acid The methylparaben, propylparaben and sodium benzoate together constitutes a preservative system. The dextrose and the fructose constitute sweeteners. Alternatively, only 0.2% sodium benzoate may be used as a preservative system.

This composition provides an agreeably sweet, smooth slurry since the sweeteners tend to coat the gritty charcoal particles.

The slurry container 10 is preferably packaged with an opaque plastic straw 30 and a plastic container of approximately one ml of flavoring fluid 32. The container 10, the straw 30 and the flavoring container 32 may be enclosed in a clear plastic sealed bag or the straw 30 and flavoring container 32 may be adhesively and removably secured to the container 10. The flavor container 32 contains the liquid artificial flavor, preferably a fruit flavor. The flavor container 32 has a conical tip 34 which may be removed and the end then inserted into the straw 30 so that the flavoring material is dispensed into the straw.

The flavoring material has a controlled viscosity which is sufficiently low to allow the material to be dispensed and to flow over a substantial portion of the interior of the straw. The viscosity is sufficiently high that the flavoring fluid coats the interior of the straw. This operation is illustrated in FIG. 2.

The viscosity of the flavoring is preferably measured using the Brookfield system per ASTM D 2196-86 (1991). This measurement produces a shear thinning index which is the ratio of the viscosity of the material at shearing rotation of 20 rpm to the viscosity of the material at a shearing rotation of 100 rpm. The shear thinning index is preferably between about 1 and 3 Flavorings with shearing indexes below 1 are too thin to coat the straw and shearing indexes above 3 are too viscous to flow over the straw. Shearing indexes in the range of 2-3 were found acceptable.

The tip 24 of the slurry container 10 is then cut off and the straw 30 is inserted into the slurry container. The flavor container tip 34 is removed from flavor container 32 and it is inserted into straw 30 and squeezed to internally coat the straw with the flavoring material. The patient then drinks the slurry by drawing it up through the straw, as illustrated in FIG. 3. The sucking action induces flow of the flavoring material into the patient's mouth. While some of the flavoring material may directly contact the charcoal slurry and bind with it, substantial portions of the flavoring material will be drawn into the patient's mouth. The combination of the pleasant flavoring material and the sweetened slurry produce a palatable mixture. Since the container and the straw are opaque the patient does not observe the unpleasant color of the material.

An alternative composition for the slurry, containing sorbitol, which acts as a cathartic, is as follows:

1) DI water 75ml

2) Dissolve methylparaben NF 0.228%, propylparaben NF 0.112% sodium benzoate NF 0.10% or 0.2% sodium benzoate 3) 70% sorbitol USP solution 60ml 4) Dextrose 34gms 5) Fructose 24gms 6) Charcoal 50gms 7) QS water to 240 ml 8) Titrate with citric acid to pH of 4.0

This slurry is administered in exactly the same manner as the preferred embodiment.

Having thus described my invention, I claim:

1. The therapeutic method of providing a patient who has ingested a toxic substance with an activated charcoal slurry comprising:

providing a quantity of activated charcoal slurry in a container;

providing a straw which may be used by the patient to orally draw up and ingest the contains of the slurry container;

providing a container of flavoring material having sufficient viscosity as to be substantially retained on the inner surface of said straw when applied within said straw;

inserting the straw into said container of charcoal slurry; and applying the flavoring to the interior of said straw so as to coat the straw with the flavoring material, drinking the charcoal slurry through the flavored coated straw so that both the flavoring and the slurry are ingested by the patient giving the slurry a flavored taste.

2. The therapeutic method of claim 1 in which the charcoal slurry includes sweeteners.

3. The therapeutic method of claim 2 in which the sweetener constitutes sugars.

4. The therapeutic method of claim 2 in which the sweetener constitutes a non-sugar synthetic.

5. The therapeutic method of claim 4 in which the non-sugar synthetic constitutes sorbitol.

6. The therapeutic method of claim 1 in which the slurry container and the straw are opaque.

7. The therapeutic method of claim 1 in which the slurry is acidic.

\* \* \* \* \*